(12) United States Patent
Tomisaki

(10) Patent No.: US 8,019,041 B2
(45) Date of Patent: Sep. 13, 2011

(54) X-RAY DIAGNOSIS APPARATUS

(75) Inventor: Takayuki Tomisaki, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 85 days.

(21) Appl. No.: 12/647,228

(22) Filed: Dec. 24, 2009

(65) Prior Publication Data

US 2010/0166146 A1 Jul. 1, 2010

(30) Foreign Application Priority Data

Dec. 25, 2008 (JP) ................. 2008-331043
Dec. 25, 2008 (JP) ................. 2008-331044
Dec. 17, 2009 (JP) ................. 2009-286219

(51) Int. Cl.
*G01N 23/04* (2006.01)
*G01N 23/06* (2006.01)

(52) U.S. Cl. ............................. 378/62; 378/51

(58) Field of Classification Search ............... 378/4, 19, 378/51, 62, 64, 65, 193, 195, 196, 208
See application file for complete search history.

(56) References Cited

U.S. PATENT DOCUMENTS 5,038,371 A * 8/1991 Janssen et al. ............... 378/197
6,609,826 B1 * 8/2003 Fujii et al. ................. 378/198
7,515,677 B2 * 4/2009 Zellerhoff ................... 378/4
2002/0159564 A1 10/2002 Wang et al.
2008/0226028 A1 * 9/2008 Ross et al. ................. 378/58

FOREIGN PATENT DOCUMENTS

JP 2004-242928 9/2004

* cited by examiner

*Primary Examiner* — Irakli Kiknadze
(74) *Attorney, Agent, or Firm* — Oblon, Spivak, McClelland, Maier & Neustadt, L.L.P.

(57) ABSTRACT

An X-ray tube generates X-rays. A detector detects X-rays generated by the X-ray tube and transmitted through a subject. A C-arm is equipped with the X-ray tube and the detector. An arm support mechanism rotatably supports the C-arm. A top is on which the subject is placed. A bed supports the top so as to change a relative positional relationship along a horizontal direction between the C-arm and the top. The bed supports the top so as to change a relative positional relationship along a vertical direction between the C-arm and the top. A mechanism control unit controls the arm support mechanism and the bed so as to a perpendicular extending from a focus of the X-ray tube intersects the top at a predetermined position thereon, and a distance interval between the X-ray tube and the predetermined position is fixed during rotation of the C-arm.

13 Claims, 12 Drawing Sheets

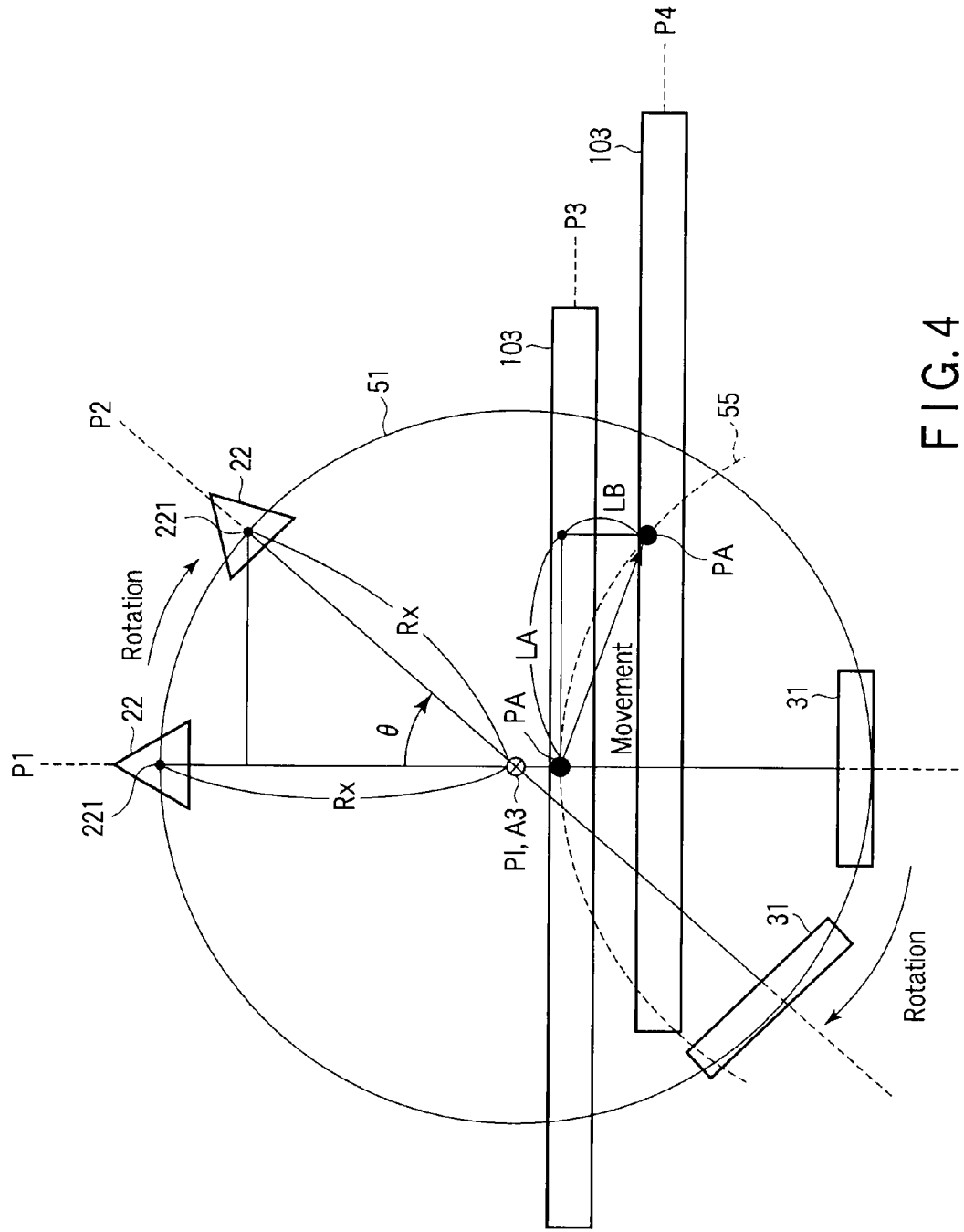
F I G. 4

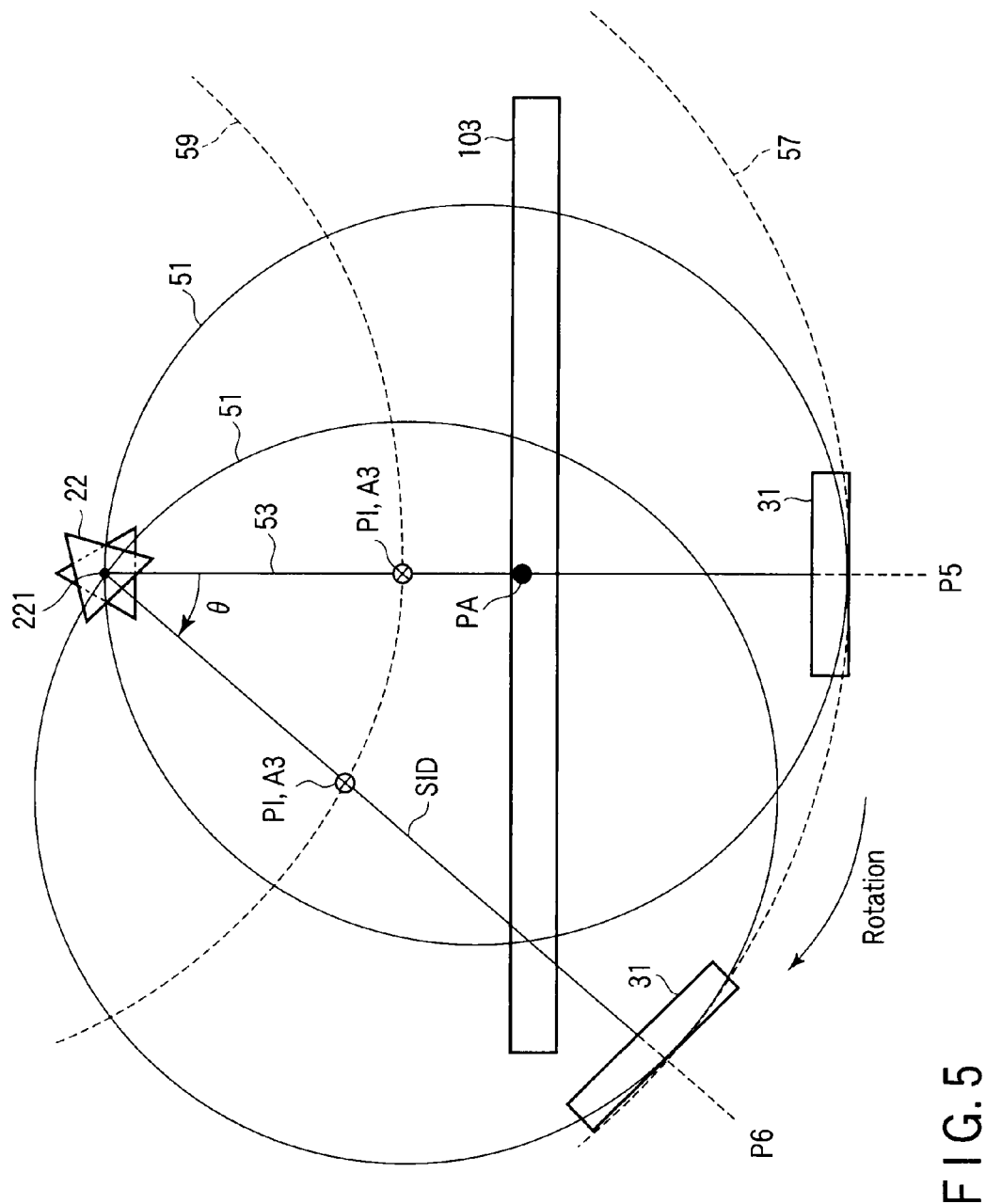
F I G. 5

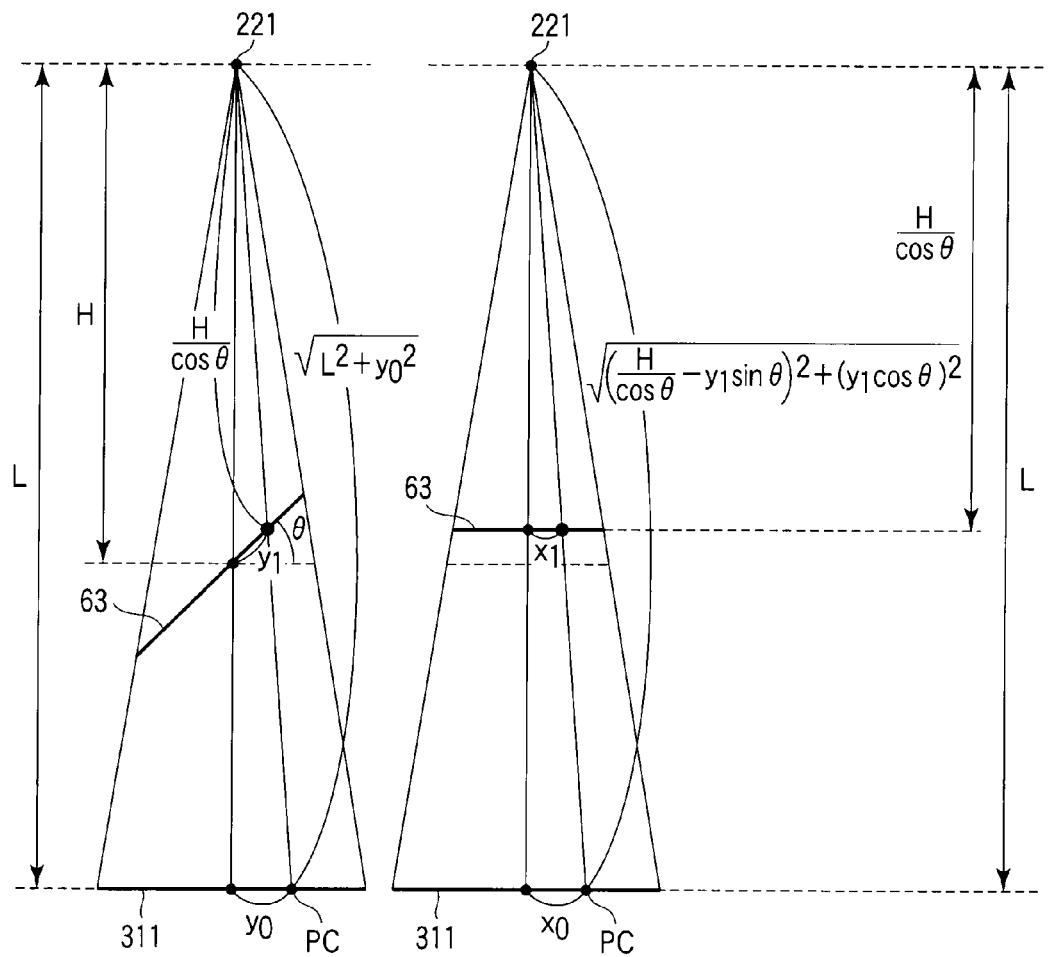
FIG. 8        FIG. 9
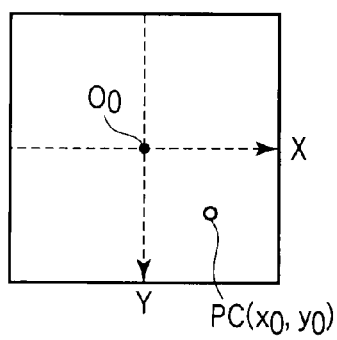
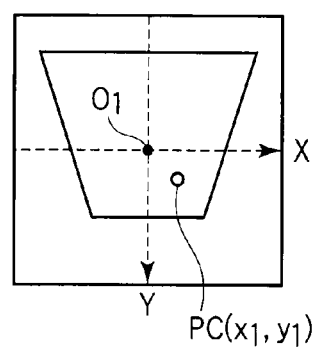
FIG. 10        FIG. 11

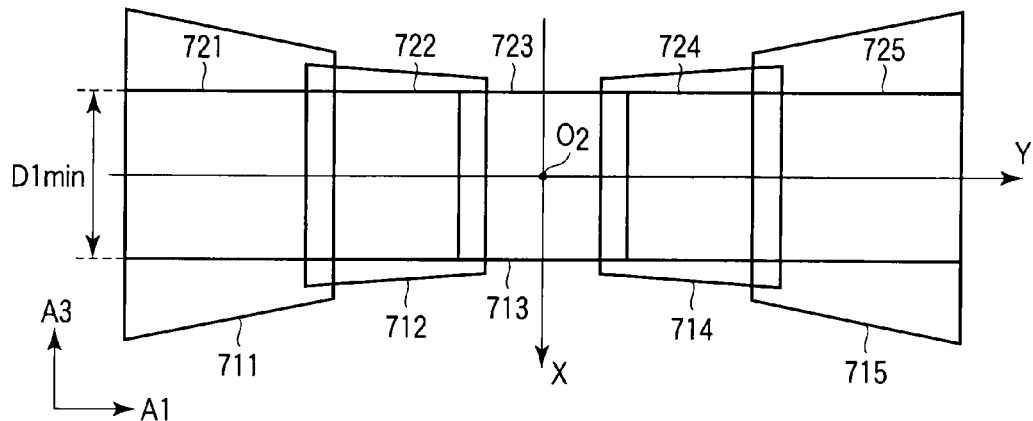
F I G. 12
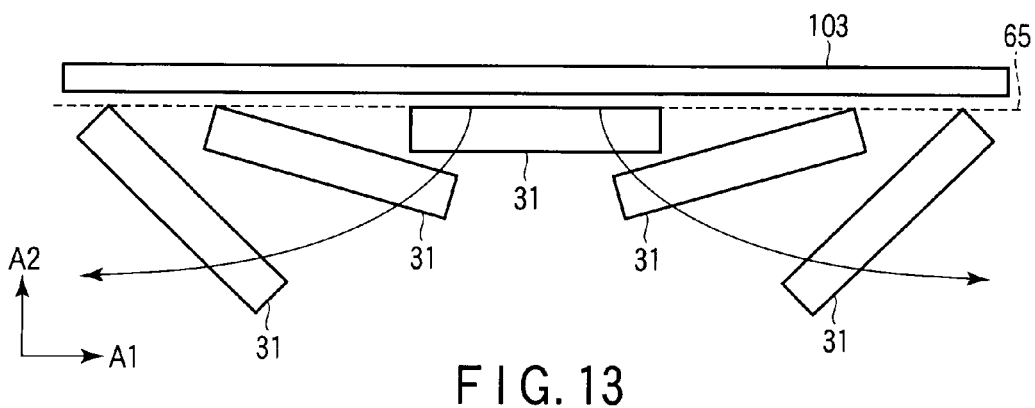
F I G. 13
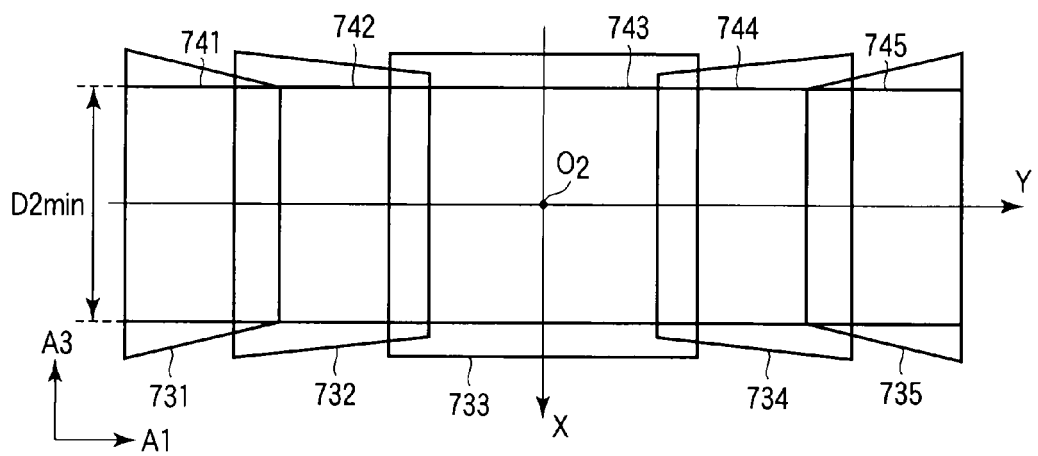
F I G. 14

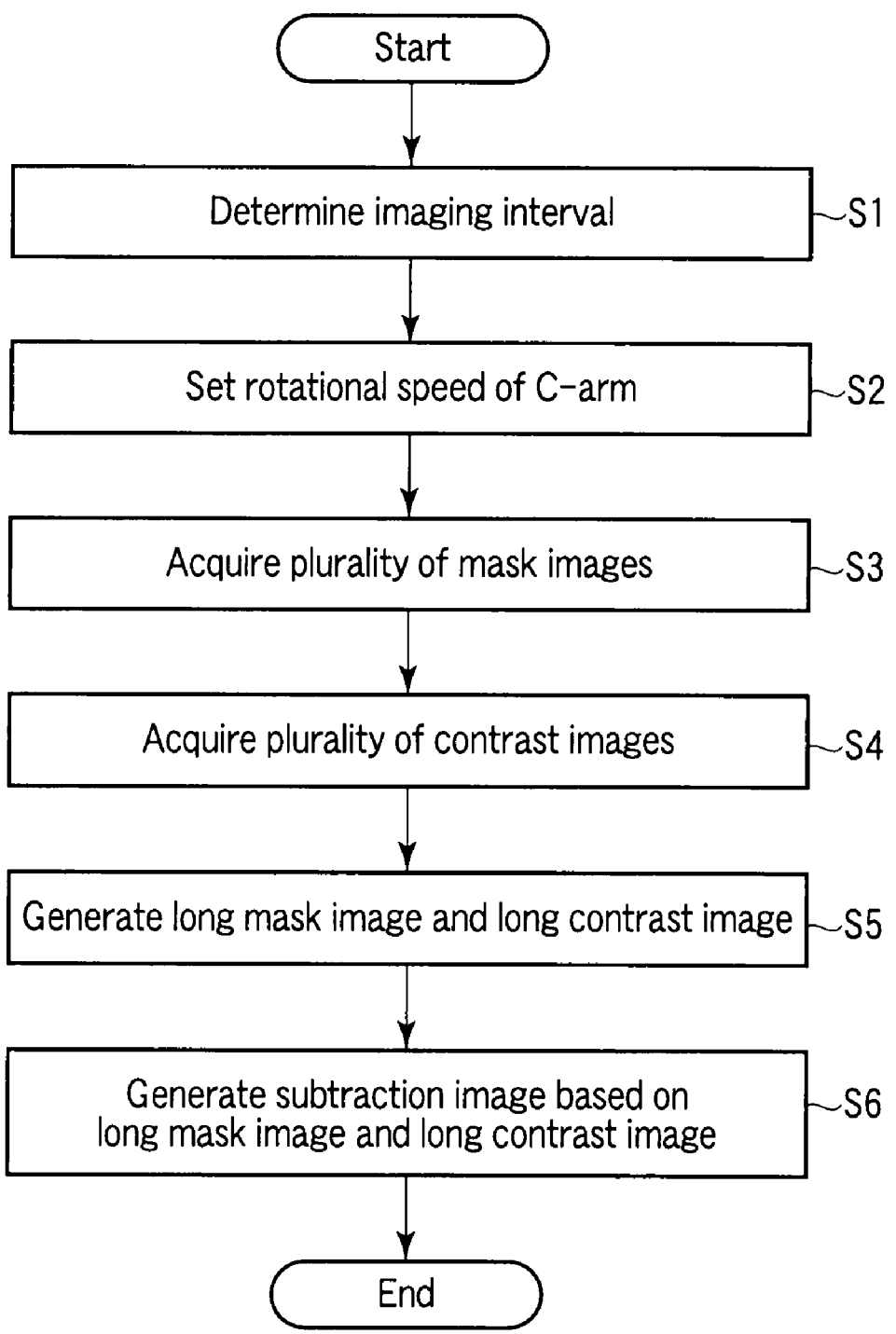
F I G. 16

X-RAY DIAGNOSIS APPARATUS

CROSS-REFERENCE TO RELATED APPLICATIONS

This application is based upon and claims the benefit of priority from prior Japanese Patent Applications No. 2008-331043, filed Dec. 25, 2008; No. 2008-331044, filed Dec. 25, 2008; and No. 2009-286219, filed Dec. 17, 2009, the entire contents of all of which are incorporated herein by reference.

BACKGROUND OF THE INVENTION

1. Field of the Invention

The present invention relates to an X-ray diagnosis apparatus which performs bolus DSA (Digital Subtraction Angiography) imaging and stepping DSA imaging of a subject.

2. Description of the Related Art

An X-ray diagnosis apparatus performs DSA imaging. In DSA imaging, a mask image is subtracted from a contrast image to generate a subtraction image with a contrast-enhanced blood vessel portion being emphasized. A contrast image is an image acquired during the inflow of a contrast medium. A mask image is an image acquired before the injection of the contrast medium. In bolus DSA imaging and stepping DSA imaging, for example, the X-ray diagnosis apparatus acquires a plurality of mask images while intermittently moving the C-arm or the bed along the body axis direction of a subject. The X-ray diagnosis apparatus then generates a long mask image by combing the plurality of mask images. The X-ray diagnosis apparatus acquires a plurality of contrast images at the same imaging positions as those of the mask images while moving the C-arm or the bed in the same manner. The X-ray diagnosis apparatus generates a long contrast image by combing the plurality of contrast images. The X-ray diagnosis apparatus then generates a long subtraction image by subtracting the long mask image from the long contrast image.

In this method, the relative positional relationships between X-ray focuses at the time of the acquisition of the respective mask images (or the respective contrast images) vary. A relative positional relationship indicates, for example, X-ray focus positions relative to a subject. Such different positional relationships will make geometric enlargement ratios of the respective images differ from each other. Due to the differences in geometric enlargement ratio, pieces of information in the thickness direction of the subject interchange on the images. For example, as shown in FIG. 17, regions Pa and Pb at different positions in the thickness direction interchange on the images. That is, the positional relationship between points $Pa_1$ and $Pb_1$ extracted on an image I1 concerning an X-ray focus position F1 interchanges with the positional relationship between points $Pa_2$ and $Pb_2$ extracted on an image I2 concerning an X-ray focus position F2. Note that the points $Pa_1$ and $Pa_2$ originate from the region Pa, and the points $Pb_1$ and $Pb_2$ originate from the region Pb. It is theoretically impossible to accurately combine images with interchanged positional relationships.

As disclosed in, for example, Jpn. Pat. Appln. KOKAI Publication No. 2004-242928, there is available a technique of acquiring images while spatially fixing an X-ray focus position, changing an X-ray irradiation direction, and moving an X-ray detector. Using this technique prevents pieces of information in the thickness direction of a subject from interchanging on images. In other words, a geometric enlargement ratio does not change. As shown in FIG. 18, for example, consider images I3 and I4 with the same X-ray focus position and different X-ray irradiation directions. In this case, the positional relationship between points $Pa_3$ and $Pb_3$ on the image I3 does not interchange with the positional relationship between points $Pa_4$ and $Pb_4$ on the image I4. Note that the points $Pa_3$ and $Pa_4$ originate from the region Pa, and the points $Pb_3$ and $Pb_4$ originate from the region Pb. It is therefore possible to easily combine the images I3 and I4.

In DSA imaging as well, using the conventional method makes it necessary, for the following reason, to acquire mask images and contrast images at the same imaging position. When an X-ray focus position concerning a mask image differs from an X-ray focus position concerning a contrast image, the information of a subject thickness on the mask image differs from that on the contrast image. In other words, the geometric enlargement ratio of the mask image differs from that of the contrast image. Along with this difference, the positioning accuracy between the mask image and the contrast image degrades, and the difference accuracy between the mask image and the contrast image degrades. This makes it necessary to obtain a mask image and a contrast image at the same position.

BRIEF SUMMARY OF THE INVENTION

It is an object of the present invention to provide an X-ray diagnosis apparatus which can perform radiography easily.

According to a first aspect of the present invention, an X-ray diagnosis apparatus includes: an X-ray tube which generates X-rays; a detector which detects X-rays generated by the X-ray tube and transmitted through a subject; a C-arm which is equipped with the X-ray tube and the detector; an arm support mechanism which rotatably supports the C-arm; a top on which the subject is placed; a first moving mechanism which supports the C-arm or the top so as to change a relative positional relationship along a horizontal direction between the C-arm and the top; a second moving mechanism which supports the C-arm or the top so as to change a relative positional relationship along a vertical direction between the C-arm and the top; and a control unit which controls the arm support mechanism, the first moving mechanism, and the second moving mechanism so as to a perpendicular extending from a focus of the X-ray tube intersects the top at a predetermined position thereon, and a distance interval between the X-ray tube and the predetermined position is fixed during rotation of the C-arm.

According to a second aspect of the present invention, an X-ray diagnosis apparatus includes: an X-ray tube which generates X-rays; a detector which detects X-rays generated from the X-ray tube and transmitted through a subject; a C-arm which is equipped with the X-ray tube and the detector; an arm support mechanism which rotatably supports the C-arm; a top on which the subject is placed; a first moving mechanism which supports the C-arm or the top so as to change a relative positional relationship along a horizontal direction between the C-arm and the top; a second moving mechanism which supports the C-arm or the top so as to change a relative positional relationship along a vertical direction between the C-arm and the top; and a control unit which controls the arm support mechanism, the first moving mechanism, and the second moving mechanism so as to when a specific instruction is received from an operator, a perpendicular extending from a focus of the X-ray tube always intersects the top at a predetermined position thereon, a distance interval between the X-ray tube and the predetermined position is fixed, and the position of the focus is fixed in a space.

According to a third aspect of the present invention, an X-ray diagnosis apparatus includes: an X-ray tube which generates X-rays; a detector which detects X-rays generated from the X-ray tube and transmitted through a subject; a top on which the subject is placed; a C-arm which is equipped with the X-ray tube and the detector; an arm support mechanism which rotatably supports the C-arm; a moving mechanism which supports the C-arm or the top so as to change a relative positional relationship along a vertical direction between the C-arm and the top; an image processing unit which generates a long mask image by combining a plurality of mask images acquired via the detector, generates a long contrast image by combining a plurality of contrast images acquired via the detector, and generates a subtraction image based on the long mask image and the long contrast image; and a control unit which controls the arm support mechanism and the moving mechanism so as to fix a focus position of the X-ray tube, move the detector on an arc orbit at a predetermined distance from the focus position, and make imaging positions of the plurality of mask images and the plurality of contrast images differ from each other.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with general description given above and the detailed description of the embodiments given below, were to explain the principles of the invention.

FIG. 4 is a view for explaining the first imaging operation mode in FIG. 3 in more detail;

FIG. 5 is a view for explaining the movement of the X-ray diagnosis apparatus in the second imaging operation mode by the mechanism control unit in FIG. 1;

FIG. 8 is a view showing the positional relationship between a detection surface and a reference plane concerning the long axis (y-axis) of a top;

FIG. 9 is a view showing the positional relationship between the detection surface and the reference plane concerning the abscissa (x-axis) of the top;

FIG. 10 is a view showing the position of a specific pixel on a detection surface coordinate system;

FIG. 11 is a view showing the position of the specific pixel on a reference plane coordinate system;

FIG. 12 is a view for explaining image combing processing;

FIG. 13 is a view showing the disposition relationship between a flat panel detector and a top in the operation of bringing the flat panel detector near to the top;

FIG. 14 is a view for explaining image combing processing in the operation of bringing the flat panel detector near to the top;

FIG. 16 is a flowchart for explaining a typical procedure of operation of the X-ray diagnosis apparatus in bolus DSA;

DETAILED DESCRIPTION OF THE INVENTION

The embodiments of the present invention will be described below with reference to the views of the accompanying drawing.

First Embodiment

Figure 1:
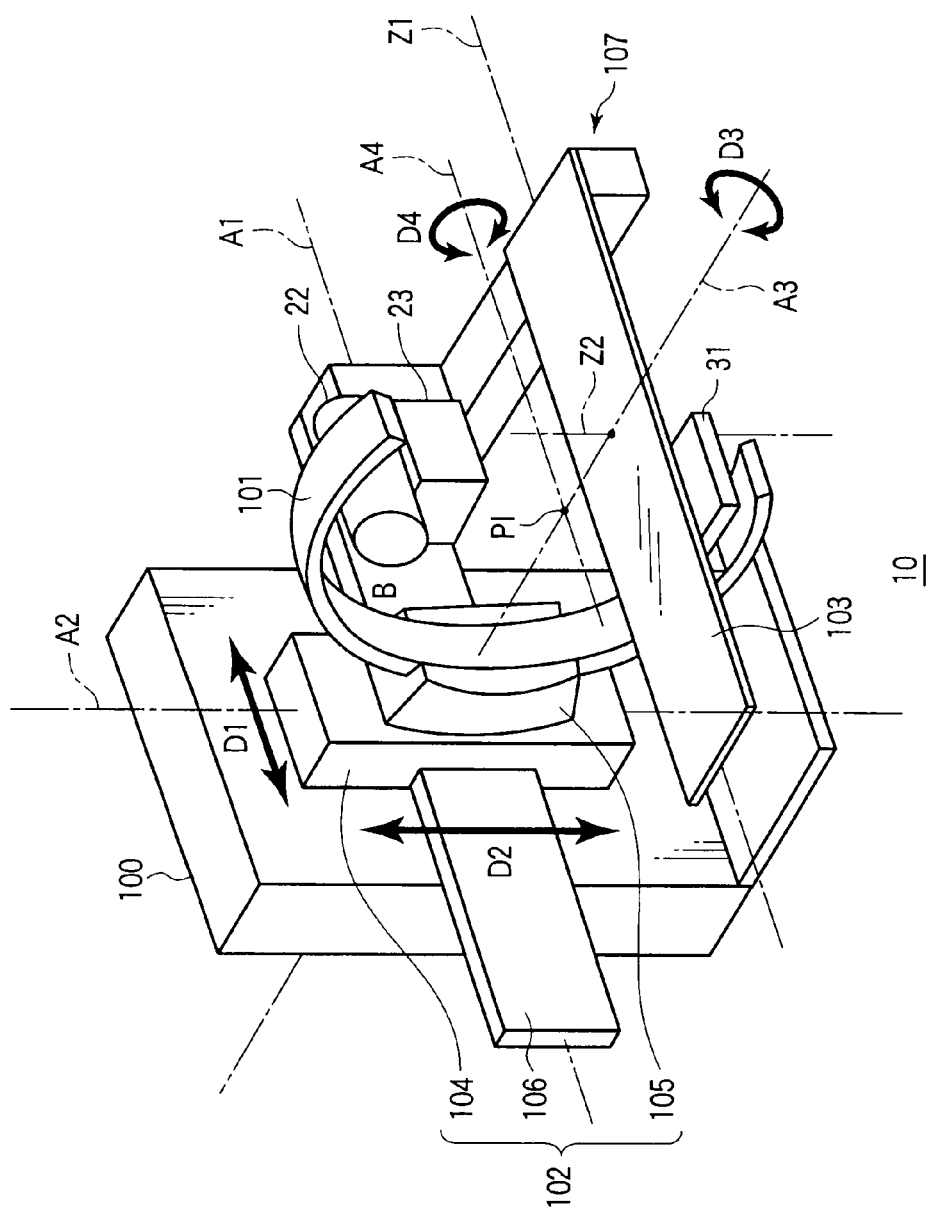
FIG. 1 is a perspective view of an X-ray diagnosis apparatus according to the first embodiment of the present invention.
Figure 2:
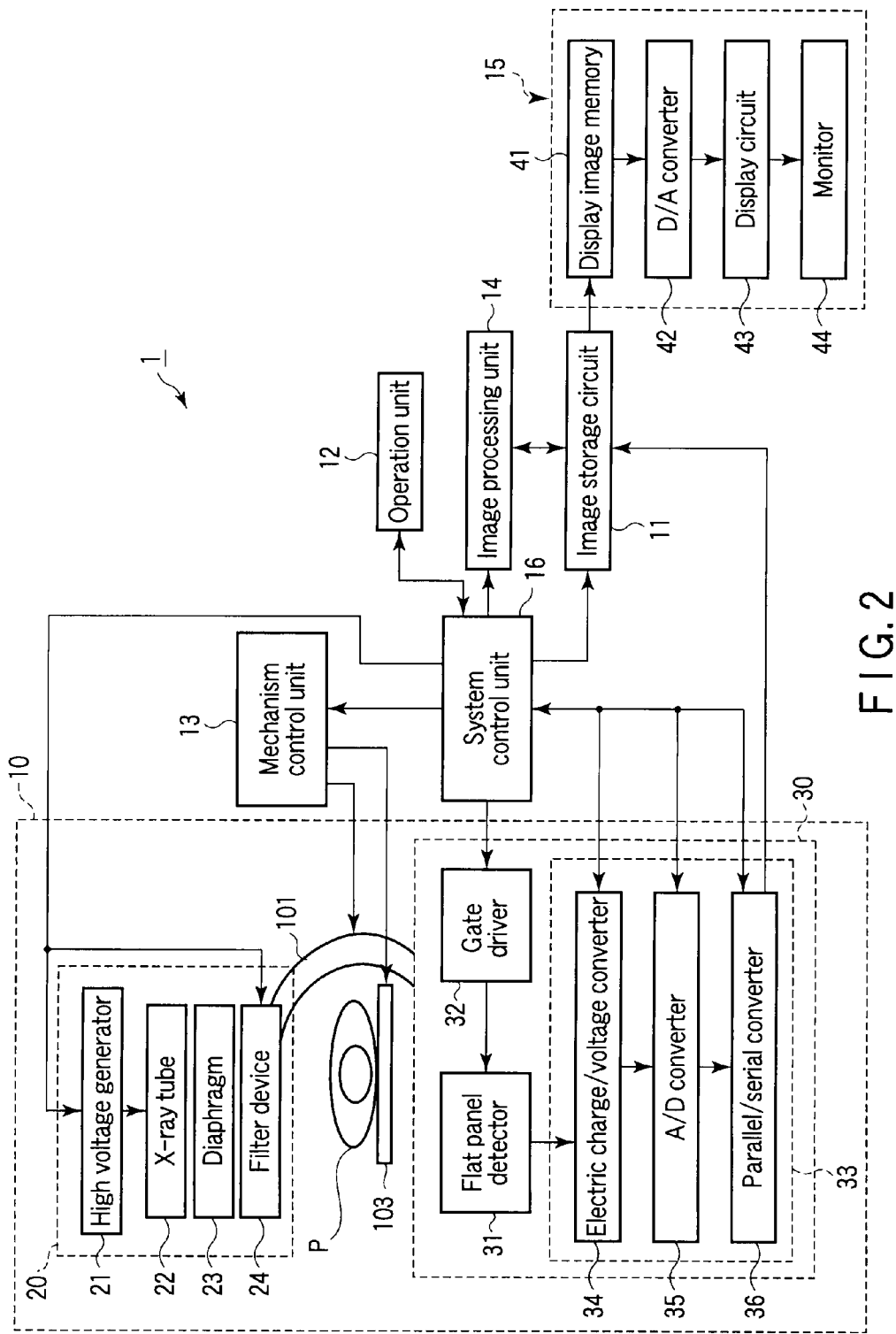
FIG. 2 is a functional block diagram of the X-ray diagnosis apparatus in FIG. 1.

FIG. 1 is a perspective view of an X-ray diagnosis apparatus according to the first embodiment. FIG. 2 is a block diagram of the X-ray diagnosis apparatus.

As shown in FIGS. 1 and 2, an X-ray diagnosis apparatus 1 includes an imaging mechanism 10, an image storage circuit 11, an operation unit 12, a mechanism control unit 13, an image processing unit 14, a display unit 15, and a system control unit 16.

The imaging mechanism 10 includes a gantry 100. The gantry 100 is installed on a floor surface. The gantry 100 includes a C-arm holder 102 to rotatably and movably support a C-arm 101. More specifically, the C-arm holder 102 supports the C-arm 101 so as to allow it to move along a horizontal axis A1 parallel to a long axis Z1 of a top 103 (direction D1), move along an axis A2 almost perpendicular to the axis A1 (direction D2), rotate about a horizontal axis A3 almost perpendicular to the axes A1 and A2 (direction D3), and move around an axis A4 almost perpendicular to the axis A3 (direction D4). The intersection between the axes A3 and A4 is called a rotation center PI (isocenter) of the C-arm 101 in the directions D3 and D4. The rotation center PI is included in a plane (C-arm plane) formed by the C-arm 101. The axis A4 coincides with the normal to the C-arm plane which passes through the rotation center PI.

More specifically, the C-arm holder 102 includes a C-arm moving mechanism 104, a C-arm rotating mechanism 105, and a slider 106. The slider 106 is placed along the axis A1. The C-arm moving mechanism 104 moves along the slider 106 (direction D1) under the control of a mechanism control unit 13. In other words, the C-arm moving mechanism 104 supports the C-arm 101 so as to allow it to change a relative positional relationship along the direction D1 (direction along the long axis Z1) between the C-arm 101 and the top 103. The C-arm moving mechanism 104 also supports the C-arm rotating mechanism 105 so as to allow it to move along the axis A2. The C-arm moving mechanism 104 moves the C-arm rotating mechanism 105 up and down along the axis A2 (direction D2) under the control of the mechanism control unit 13. In other words, the C-arm moving mechanism 104 supports the C-arm 101 so as to allow it to change a relative positional relationship along the direction D2 (direction along vertical axis Z2) between the C-arm 101 and the top 103. The C-arm moving mechanism 104 supports the C-arm rotating mechanism 105 so as to allow it to rotate about the horizontal axis A3. The C-arm moving mechanism 104 rotates the C-arm rotating mechanism 105 about the horizontal axis A3 (direction D3) under the control of the mechanism control unit 13. The C-arm rotating mechanism 105 supports the C-arm 101 so as to allow it to slide around the axis A4. The C-arm rotating mechanism 105 slides the C-arm 101 around the axis A4 (direction D4) under the control of the mechanism control unit 13. With this operation, the C-arm 101 slides along the C shape.

The C-arm 101 is equipped with an X-ray generating unit 20 and an X-ray detection unit 30.

The X-ray generating unit 20 includes a high voltage generator 21, an X-ray tube 22, a diaphragm 23, and a filter device 24. The high voltage generator 21 applies a tube voltage and supplies a filament current to the X-ray tube 22 under the control of the system control unit 16. Upon receiving the tube voltage and filament current from the high voltage generator 21, the X-ray tube 22 generates X-rays. The diaphragm 23 blocks X-rays emitted from the X-ray tube 22 to limit an X-ray irradiation field. The filter device 24 switchably includes, for example, the first filter for acquiring images concerning high energy and the second filter for acquiring images concerning low energy. The filter device 24 switches the first filter and the second filter under the control of the system control unit 16.

The X-ray detection unit 30 detects the X-rays generated from the X-ray tube 22 and transmitted through the subject P and generates image data corresponding to the intensity of the detected X-rays under the control of the system control unit 16. More specifically, the X-ray detection unit 30 includes a flat panel detector 31, a gate driver 32, and an image data generating unit 33. The flat panel detector 31 detects the X-rays generated from the X-ray tube 22 and transmitted through the subject P and generates electric charges corresponding to the intensity of the detected X-rays. The gate driver 32 reads out the electric charges generated by the flat panel detector 31 and supplies the read electric charges to the image data generating unit 33. The image data generating unit 33 includes an electric charge/voltage converter 34, an A/D converter 35, and a parallel/serial converter 36. The electric charge/voltage converter 34 converts the read electric charges into a voltage. The A/D converter 35 A/D-converts the voltage to generate image data. The generated image data is supplied (acquired) to the image storage circuit 11 via the parallel/serial converter 36.

As shown in FIG. 1, the imaging mechanism 10 includes a bed 107. The bed 107 supports the top 103 so as to allow it to move along the long axis Z1 and the vertical axis Z2. The long axis Z1 extends along the longitudinal direction of the top 103. The vertical axis Z2 extends along the vertical direction. The vertical axis Z2 is defined by, for example, the normal to the top 103. The subject P is placed on the top 103. The bed 107 moves the top 103 along the long axis Z1 and the vertical axis Z2 under the control of the mechanism control unit 13. In other words, the bed 107 supports the top 103 so as to allow it to change a relative positional relationship along the direction D1 (direction along long axis Z1) between the C-arm 101 and the top 103. In addition, the bed 107 supports the top 103 so as to allow it to change a relative positional relationship along the direction D2 (direction along vertical axis Z2) between the C-arm 101 and the top 103.

The operation unit 12 is provided on, for example, the bed 107. The operation unit 12 includes various switches and devices such as a joystick for rotating and moving the C-arm 101. The operation unit 12 generates an operation signal corresponding to device operation by an operator, and supplies the generated operation signal to the system control unit 16.

The mechanism control unit 13 controls the C-arm holder 102 and the bed 107 in accordance with instructions issued by the operator via the operation unit 12 or under the control of the system control unit 16. The mechanism control unit 13 controls the C-arm holder 102 and the bed 107 so as to make the geometric enlargement ratios of acquired images almost equal to each other regardless of imaging positions. More specifically, the mechanism control unit 13 controls the C-arm moving mechanism 104 to slide the C-arm 101 along the axis A1. With this control, the X-ray tube 22 and the flat panel detector 31 slide along the direction D1. The mechanism control unit 13 controls the C-arm moving mechanism 104 to move the C-arm 101 up and down along the axis A2. With this control, the X-ray tube 22 and the flat panel detector 31 move up and down along the direction D2. The mechanism control unit 13 also controls the C-arm moving mechanism 104 to slide the C-arm 101 around the axis A3. With this control, the X-ray tube 22 and the flat panel detector 31 rotate along the direction D3. The mechanism control unit 13 controls the C-arm rotating mechanism 105 to slide the C-arm 101 around the axis A4. With this control, the X-ray tube 22 and the flat panel detector 31 slide in the direction D4. The mechanism control unit 13 controls the bed 107 to slide the top 103 along the long axis Z1. With this control, the top 103 slides along the longitudinal direction. The mechanism control unit 13 controls the bed 107 to move the top 103 up and down along the vertical axis Z2. With this control, the top 103 moves up and down along the vertical direction. A concrete control method will be described later.

The image processing unit 14 reads out image data stored in the image storage circuit 11 and image-processes the read image data. For example, the image processing unit 14 combines a plurality of images in accordance with the imaging positions. The image storage circuit 11 stores the image-processed image data.

The display unit 15 includes a display image memory 41, a D/A converter 42, a display circuit 43, and a monitor 44. The display image memory 41 temporarily stores image data to be displayed. The D/A converter 42 analog-converts the image data in the display image memory 41 to generate a display image signal. The display circuit 43 processes the display image signal. The monitor 44 displays an image represented by the processed display image signal. The operator performs X-ray diagnosis/treatment by operating the operation unit 12 while checking the image and the like displayed on the monitor 44. Note that the display unit 15 typically includes a plurality of monitors 44.

The system control unit 16 functions as the main unit of the X-ray diagnosis apparatus 1. The system control unit 16 controls the respective components of the X-ray diagnosis apparatus 1 to radiograph a subject.

The operation of the X-ray diagnosis apparatus 1 at the time of radiography will be described next. The X-ray diagnosis apparatus 1 selectively executes the first imaging operation mode and the second imaging operation mode under the control of the mechanism control unit 13. In the first imaging operation mode, the X-ray tube 22, the flat panel detector 31, and the top 103 rotate and move. In the second imaging operation mode, the top 103 is fixed, and the X-ray tube 22 and the flat panel detector 31 rotate and move. Note that the operator can arbitrarily select the first imaging operation mode and the second imaging operation mode via the operation unit 12.

The operation of the X-ray diagnosis apparatus 1 in the first imaging operation mode (in which the X-ray tube 22, the flat panel detector 31, and the top 103 rotate and move) will be described first with reference to FIG. 3.

During radiography, the mechanism control unit 13 controls the C-arm rotating mechanism 105 to rotate the C-arm 101 about the axis A3. As the C-arm 101 rotates, the X-ray tube 22 and the flat panel detector 31 rotate on a circular orbit 51. The circular orbit 51 has a rotation radius Rx centered on the rotation center PI. For example, the X-ray tube 22 and the flat panel detector 31 rotate from an imaging position P1 to an imaging position P2. As the X-ray tube 22 and the flat panel detector 31 move in this manner, the top 103 moves from a position P3 to a position P4.

As the C-arm 101 rotates, the mechanism control unit 13 controls the bed 107 to satisfy the first condition and the second condition. The first condition and the second condition concern the positional relationship to be established between the X-ray tube 22 and the top 103. More specifically, the first condition is that a perpendicular 53 extending from a focus 221 of the X-ray tube 22 always intersects the top 103 at a predetermined position PA. The predetermined position PA is, for example, the center of the top 103 in the direction D1. The second condition is that a distance interval DD between the focus 221 and the predetermined position PA is fixed. The distance interval DD is synonymous with the shortest distance between the focus 221 and the top 103. When the first condition and the second condition are satisfied, the predetermined position PA on the top 103 moves on an arc orbit 55 having the same diameter as that of the rotation radius Rx of the X-ray tube 22. When the first condition and the second condition are satisfied, the relative positional relationship between the focus 221 and the top 103 remains unchanged regardless of the rotation of the C-arm 101. In other words, the mechanism control unit 13 controls the bed 107 to make the relative positional relationship between the position of the focus 221 and the predetermined position PA remain unchanged.

Figure 3:
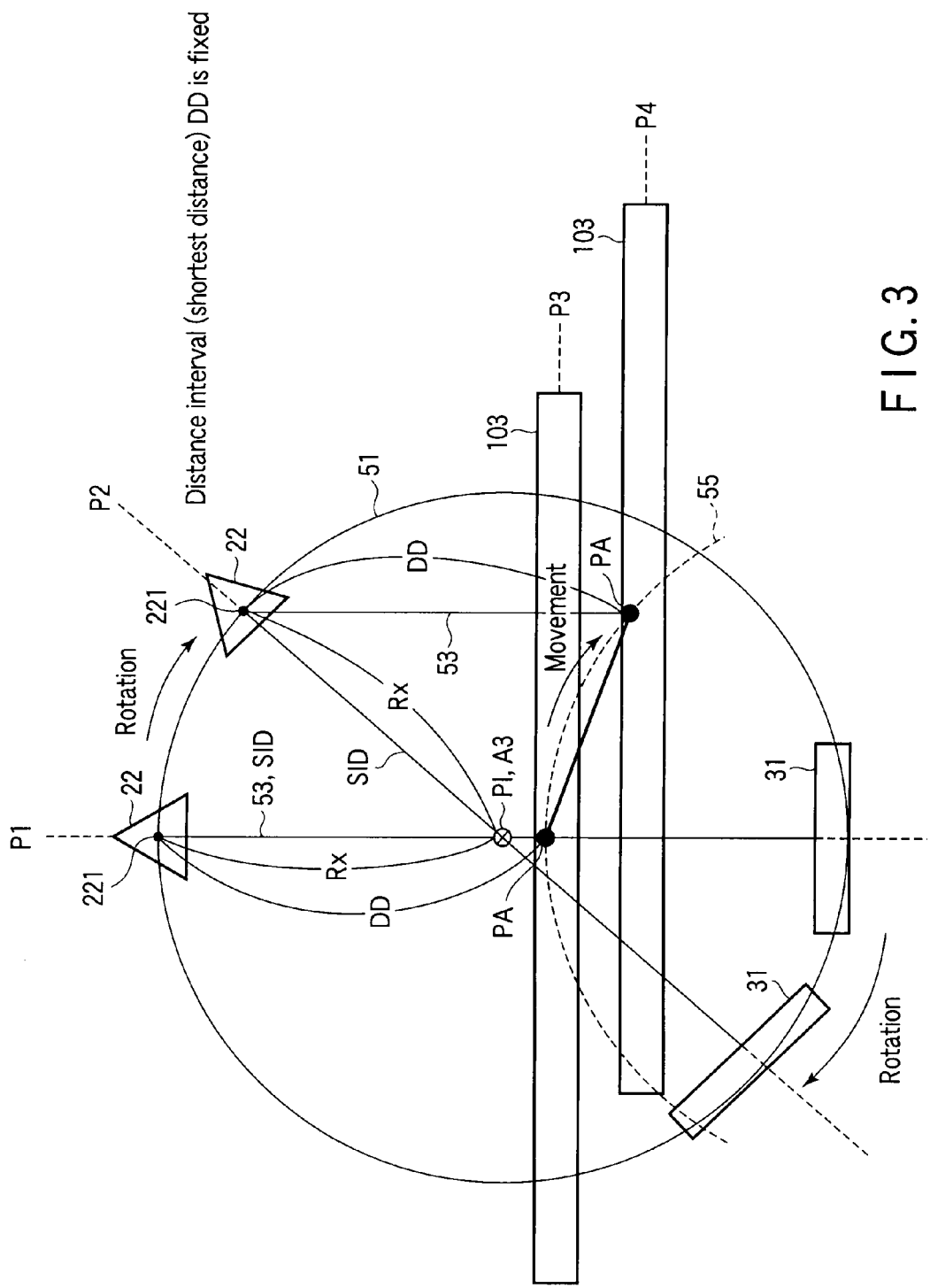
FIG. 3 is a view for explaining the movement of the X-ray diagnosis apparatus in the first imaging operation mode by a mechanism control unit in FIG. 1.

Note that FIG. 3 exemplifies the case in which the C-arm 101 rotates in the direction D1 of the top 103. However, the rotating direction of the C-arm 101 is not limited to this. That is, the rotating direction of the C-arm can be any direction.

The movement of the top 103 will be described in more detail next with reference to FIG. 4. Assume that, as shown in FIG. 4, the C-arm 101 rotates about the rotation center PI (axis A3) by a rotational angle θ. In this case, a moving distance LA in the direction D1 of the top 103 and a moving distance LB in the direction D2 of the top 103 respectively comply with $$LA = Rx \times \sin\theta \quad (1)$$

$$LB = Rx(1 - \cos\theta) \quad (2)$$

For example, the mechanism control unit 13 controls the moving distance LA and moving distance LB of the top 103 in accordance with the rotational angle θ of the C-arm 101 and the rotation radius Rx of the X-ray tube 22.

The operation of the X-ray diagnosis apparatus 1 in the second imaging operation mode (in which the top 103 is fixed and the X-ray tube 22 and the flat panel detector 31 rotate and move) will be described with reference to FIG. 5.

During radiography, the mechanism control unit 13 fixes the top 103. While the top 103 is fixed, the mechanism control unit 13 controls the bed 107 so as to satisfy the first condition, the second condition, and the third condition. The first condition and the second condition are given as described above. The third condition is that the focus 221 of the X-ray tube 22 is fixed in the real space regardless of the rotation/movement of the C-arm 101. When the first condition, the second condition, and the third condition are satisfied, the flat panel detector 31 moves on an arc orbit 57. The arc orbit 57 has a rotation center coinciding with the focus 221. The arc orbit 57 has a radius equal to the distance interval between the focus 221 and the flat panel detector 31 (a line connecting the focus 221 and the center of the detection surface of the flat panel detector 31: an imaging axis SID). The rotation center PI of the C-arm 101 moves on an arc orbit 59 having a radius shorter than the imaging axis SID (for example, almost half of SID). As a result, the X-ray tube 22 (X-ray irradiation direction) swings along the longitudinal axis Z1 of the top 103, centered on the focus 221, while the distance between the focus 221 and the top 103 is kept constant. For example, as shown in FIG. 5, when the X-ray tube 22 swings by an angle θ with the focus 221 being fixed, the flat panel detector 31 moves from an imaging position P5 to an imaging position P6 along the arc orbit 57. In addition, as in the first imaging operation mode, the relative positional relationship between the focus 221 and the predetermined position PA remains unchanged regardless of the rotation of the C-arm 101. In other words, the mechanism control unit 13 controls the C-arm holder 102 so as to make the relative positional relationship between the focus 221 and the predetermined position PA remain unchanged.

As described above, in the first imaging operation mode, the mechanism control unit 13 interlocks the operation of the C-arm 101 with the operation of the top 103 so as to perform radiography at a plurality of imaging positions along the direction D1. For this reason, even if the C-arm 101 cannot move in the direction D1, it is possible to perform radiography at a plurality of imaging positions. In the second imaging operation mode, the mechanism control unit 13 makes only the C-arm 101 operate without making the top 103 operate. For this reason, even if no moving mechanism is provided for the top 103, it is possible to perform radiography at a plurality of imaging positions. In the second imaging operation mode, the mechanism control unit 13 need not interlock the operation of the C-arm 101 with the operation of the top 103. In the second imaging operation mode, therefore, it is possible to omit complicated control for interlocking.

With the above operation, the X-ray diagnosis apparatus 1 according to the first embodiment can change the X-ray irradiation direction relative to the top 103 while fixing the relative positional relationship between the focus 221 and the top 103. Therefore, the X-ray diagnosis apparatus 1 can acquire a plurality of images which can be regarded as obtained at different imaging positions while X-rays are applied from one focus 221. The X-ray diagnosis apparatus 1 according to the first embodiment therefore need not strictly adjust imaging positions. This makes it possible to perform radiography more easily than the conventional apparatus.

In the first imaging operation mode described above, the mechanism control unit 13 controls the C-arm rotating mechanism 105 and the bed 107 so as to satisfy the first condition and the second condition. That is, during rotation of the C-arm 101, the top 103 moves in the direction D1 and the direction D2 so as to satisfy the first condition and the second condition. However, this embodiment is not limited to this. For example, in the first imaging operation mode, the mechanism control unit 13 may control the C-arm rotating mechanism 105 and the C-arm moving mechanism 104 so as to satisfy the first condition and the second condition during rotation of the C-arm 101. That is, the rotation center PI of the C-arm 101 may move in the direction D1 and the direction D2 so as to satisfy the first condition and the second condition.

When moving of the top 103 in the direction D1 is impossible, in the first imaging operation mode, the mechanism control unit 13 may control the C-arm moving mechanism 104, the C-arm rotating mechanism 105, and the bed 107 so as to satisfy the first condition and the second condition during rotation of the C-arm 101. That is, during rotation of the C-arm 101, the rotation center PI of the C-arm 101 may move in the direction D1 and the top 103 moves in the direction D2 so as to satisfy the first condition and the second condition.

In the second imaging operation mode described above, the mechanism control unit 13 controls the C-arm moving mechanism 104 and the C-arm rotating mechanism 105 so as to satisfy the first condition, the second condition, and the third condition. That is, during rotation of the C-arm 101, the C-arm 101 moves in the direction D1 and the direction D2 so as to satisfy the first condition, the second condition, and the third condition. However, this embodiment is not limited to this. For example, in the second imaging operation mode, the mechanism control unit 13 may control the C-arm moving mechanism 104 and the C-arm rotating mechanism 105 so as to satisfy the first condition, the second condition, and the third condition during rotation of the C-arm 101. That is, the rotation center PI of the C-arm 101 may move in the direction D1 and the direction D2 so as to satisfy the first condition, the second condition, and the third condition.

Alternatively, in the second imaging operation mode, the mechanism control unit 13 may control the C-arm moving mechanism 104, the C-arm rotating mechanism 105, and the bed 107 so as to satisfy the first condition, the second condition, and the third condition during rotation of the C-arm 101. That is, during rotation of the C-arm 101, the rotation center PI of the C-arm 101 may move in the direction D1 and the top 103 moves in the direction D2 so as to satisfy the first condition, the second condition, and the third condition.

Second Embodiment

An X-ray diagnosis apparatus 1 according to the second embodiment of the present invention will be described next.

Note that in the following description, the same reference numerals denote constituent elements having almost the same functions as those in the first embodiment, and a repetitive description will be made only when required.

The operation of the X-ray diagnosis apparatus 1 according to the second embodiment will be described below with reference to FIG. 6 by taking the first imaging operation mode (in which an X-ray tube 22, a flat panel detector 31, and a top 103 rotate and move) as an example. Note that a C-arm 101 supports the flat panel detector 31 so as to allow it to change the direction of a detection surface 311. The mechanism control unit 13 controls the C-arm 101 so as to always make the flat panel detector 31 parallel to a predetermined plane 61. For example, the predetermined plane 61 is defined by a plane parallel to the top 103. A perpendicular 53 from a focus 221 intersects the predetermined plane 61 at a point PB.

The C-arm 101 also supports the flat panel detector 31 so as to allow it to slide along an imaging axis SID. The mechanism control unit 13 controls the C-arm 101 to slide the flat panel detector 31 along the imaging axis SID. As the flat panel detector 31 slides along the imaging axis SID, a rotation radius R of the flat panel detector 31 is adjusted.

Figure 6:
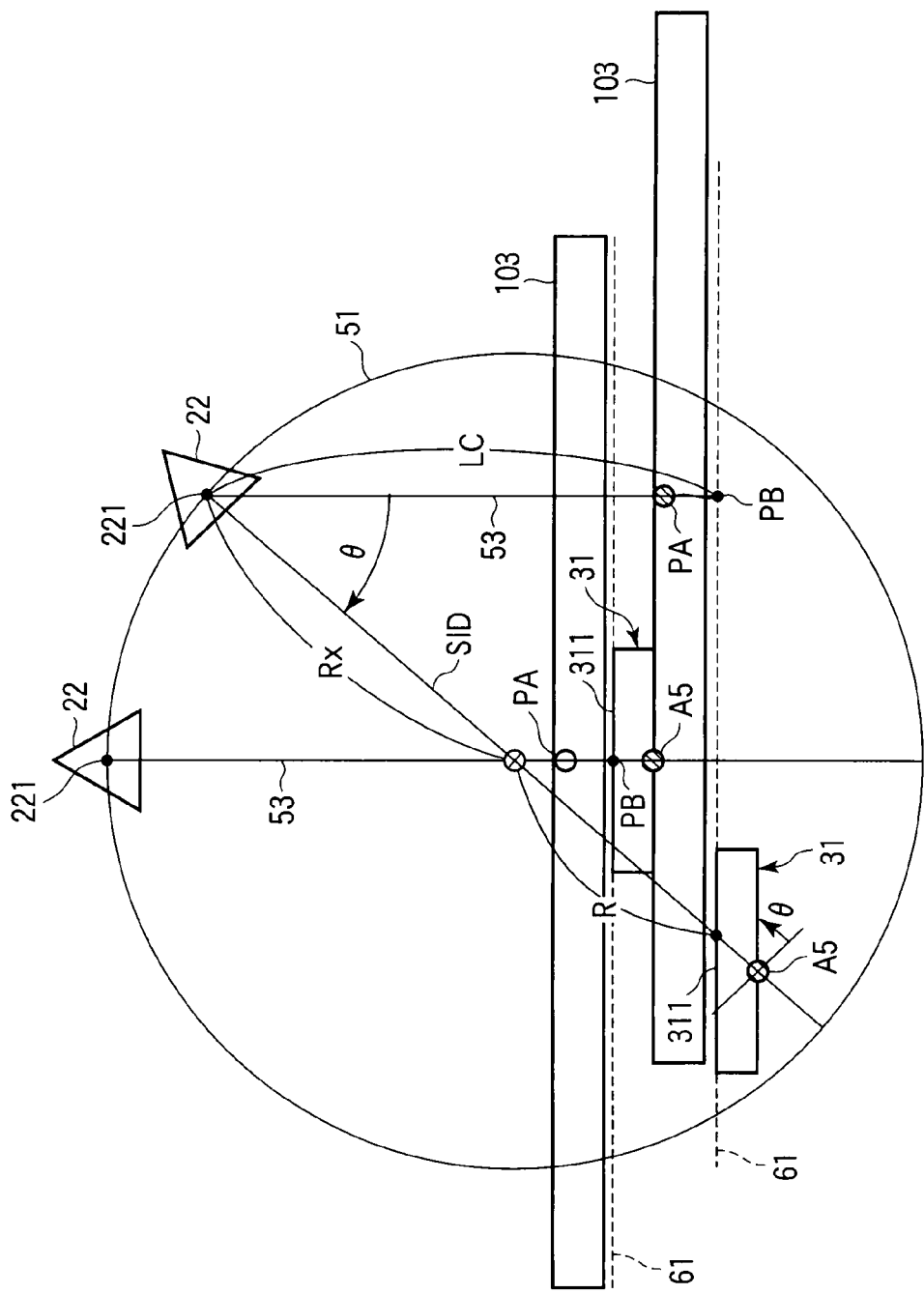
FIG. 6 is a view for explaining the movement of an X-ray diagnosis apparatus in the first imaging operation mode by the mechanism control unit in FIG. 1 according to the second embodiment of the present invention.

As shown in FIG. 6, during radiography, the mechanism control unit 13 controls the C-arm rotating mechanism 105 to rotate the C-arm 101 about an axis A3. As the C-arm 101 rotates, the X-ray tube 22 and the flat panel detector 31 rotate on a circular orbit 51 centered on the axis A3. As the C-arm 101 rotates, the mechanism control unit 13 controls a bed 107 so as to satisfy the first condition and the second condition. The mechanism control unit 13 further controls the C-arm 101 so as to always make the flat panel detector 31 parallel to the predetermined plane 61 regardless of imaging positions.

More specifically, the C-arm 101 has, on the imaging axis SID, a rotation center A5 for changing the direction of the flat panel detector 31. The flat panel detector 31 rotates about the rotation center A5 so as to always make the detection surface 311 parallel to the top 103 regardless of the rotation of the C-arm 101. Typically, the mechanism control unit 13 rotates the flat panel detector 31 so as to make a rotational angle θ of the flat panel detector 31 coincide with the angle θ defined by the perpendicular 53 and the imaging axis SID (i.e., the rotational angle θ of the C-arm 101). The mechanism control unit 13 also controls the rotation radius R and mounting angle θ of the flat panel detector 31 so as to always fix a distance interval LC between a focus 211 and the point PB regardless of the rotation of the C-arm 101 according to equation (3) given below. The mechanism control unit 13 slides the flat panel detector 31 along the imaging axis SID to adjust the rotation radius R of the flat panel detector 31. The mechanism control unit 13 rotates the flat panel detector 31 about the rotation center A5 to adjust the mounting angle θ of the flat panel detector 31.

$$R=(LC/\cos\theta)-Rx \qquad (3)$$

It is necessary to give careful consideration to the direction of the grid mounted on the flat panel detector 31. If the flat panel detector 31 is made to rotate only in the longitudinal direction of the top 103 as described above, the grid preferably has a slit parallel to a long axis Z1.

With the above operation, the X-ray diagnosis apparatus 1 according to the second embodiment controls the direction and rotation radius of the flat panel detector 31 so as to always make the detection surface 311 parallel to the top 103 regardless of the rotational angle of the C-arm 101. In addition, controlling the bed 107 in the same manner as in the first embodiment will keep the vertical distance from the X-ray tube 22 to the detection surface 311 constant. As described above, the X-ray diagnosis apparatus 1 can acquire a plurality of images with the same geometric enlargement ratio regardless of imaging positions by controlling the bed 107 and the flat panel detector 31. Since images have the same geometric enlargement ratio, an image processing unit 14 can adjust the positions of the images by only shifting pixels. That is, the image processing unit 14 can combine a plurality of images without enlarging or reducing the respective images.

The second embodiment has been described by taking the first imaging operation mode as an example. However, the second embodiment is not limited to this. The mechanism control unit 13 according to the second embodiment can execute the second imaging operation mode (in which the top 103 is fixed and the X-ray tube 22 and flat panel detector 31 rotate and move). That is, in the second imaging operation mode, the mechanism control unit 13 controls the rotation radius R and mounting angle θ of the flat panel detector 31 so as to always fix the distance interval LC between the focus 221 and the point PB regardless of the rotation of the C-arm 101 according to equation (3).

Note that in the first imaging operation mode described above, the mechanism control unit 13 controls the C-arm rotating mechanism 105 and the bed 107 so as to satisfy the first condition and the second condition. That is, during rotation of the C-arm 101, the top 103 moves in the direction D1 and the direction D2 so as to satisfy the first condition and the second condition. However, this embodiment is not limited to this. For example, in the first imaging operation mode, the mechanism control unit 13 may control the C-arm rotating mechanism 105 and the C-arm moving mechanism 104 so as to satisfy the first condition and the second condition during rotation of the C-arm 101.

When moving of the top 103 in the direction D1 is impossible, in the first imaging operation mode, the mechanism control unit 13 may control the C-arm moving mechanism 104, the C-arm rotating mechanism 105, and the bed 107 so as to satisfy the first condition and the second condition during rotation of the C-arm 101.

In the second imaging operation mode described above, the mechanism control unit 13 controls the C-arm moving mechanism 104 and the C-arm rotating mechanism 105 so as to satisfy the first condition, the second condition, and the third condition. That is, during rotation of the C-arm 101, the C-arm 101 moves in the direction D1 and the direction D2 so as to satisfy the first condition, the second condition, and the third condition. However, this embodiment is not limited to this. For example, in the second imaging operation mode, the mechanism control unit 13 may control the C-arm moving mechanism 104 and the C-arm rotating mechanism 105 so as to satisfy the first condition, the second condition, and the third condition during rotation of the C-arm 101. That is, the rotation center PI of the C-arm 101 may move in the direction D1 and the direction D2 so as to satisfy the first condition, the second condition, and the third condition.

Alternatively, in the second imaging operation mode, the mechanism control unit 13 may control the C-arm moving mechanism 104, the C-arm rotating mechanism 105, and the bed 107 so as to satisfy the first condition, the second condition, and the third condition during rotation of the C-arm 101. That is, during rotation of the C-arm 101, the rotation center PI of the C-arm 101 may move in the direction D1 and the top 103 moves in the direction D2 so as to satisfy the first condition, the second condition, and the third condition.

Third Embodiment

An X-ray diagnosis apparatus according to the third embodiment of the present invention will be described next.

Note that in the following description, the same reference numerals denote constituent elements having almost the same functions as those in the first and second embodiments, and a repetitive description will be made only when required.

The operation of the X-ray diagnosis apparatus according to the third embodiment will be described first with reference to FIG. 7 by taking the second imaging operation mode (in which a top 103 is fixed and an X-ray tube 22 and a flat panel detector 31 rotate and move) as an example.

Figure 7:
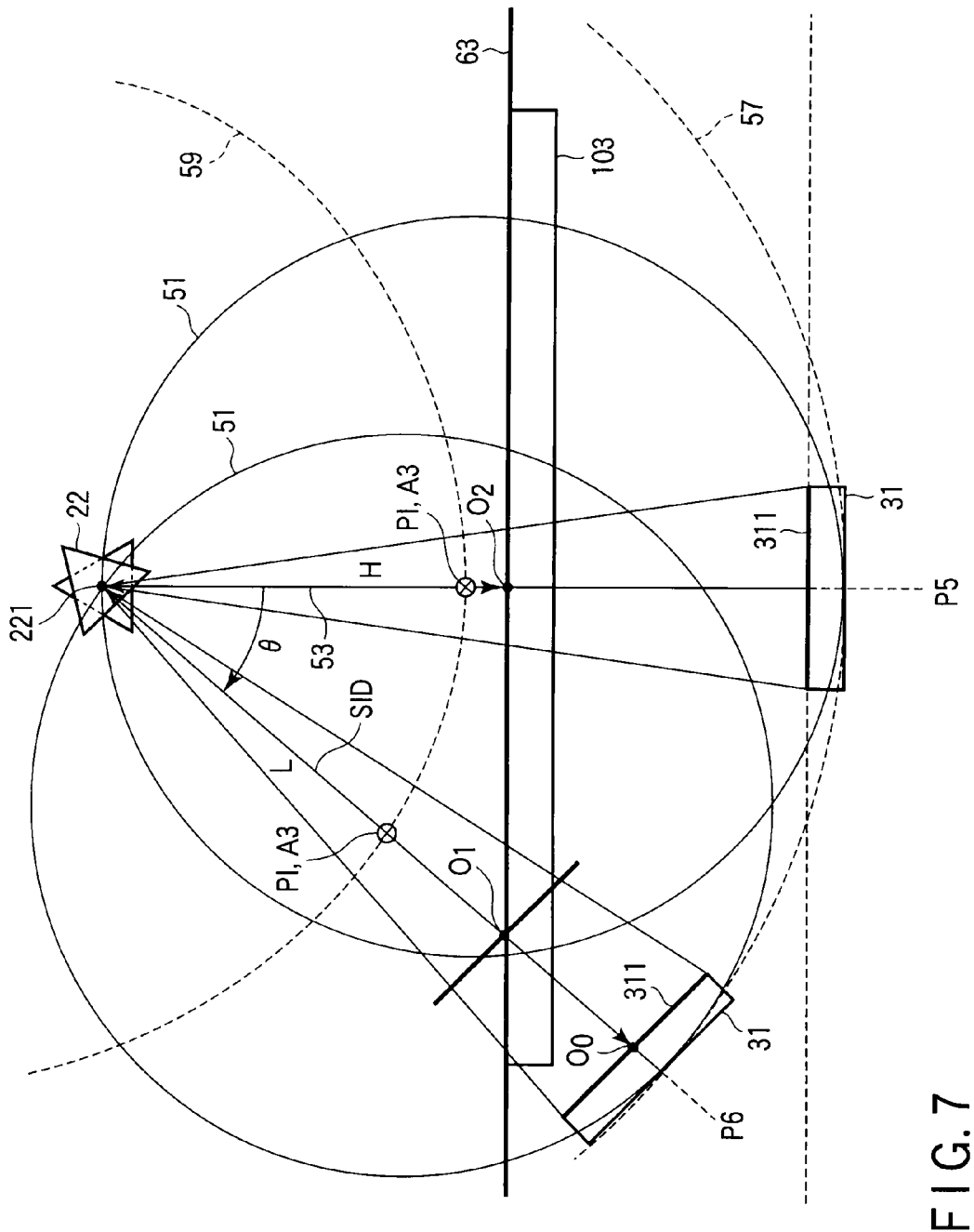
FIG. 7 is a view for explaining the movement of an X-ray diagnosis apparatus in the second imaging operation mode by the mechanism control unit in FIG. 1 according to the third embodiment of the present invention.

As shown in FIG. 7, during radiography, a mechanism control unit 13 controls the C-arm moving mechanism 104 and the C-arm rotating mechanism 105 so as to satisfy the first condition, the second condition, and the third condition. In addition, the mechanism control unit 13 fixes the flat panel detector 31 to always make a detection surface 311 perpendicular to an X-ray irradiation direction (imaging axis SID). An X-ray detection unit 30 acquires images under these conditions. An image processing unit 14 projects the acquired images onto a reference plane 63 parallel to the top 103. The reference plane 63 is a plane virtually set in the image processing space. For example, the reference plane 63 is set on the surface of the top 103, as shown in FIG. 7. Alternatively, when the flat panel detector 31 is positioned vertically below the top 103, the reference plane 63 may be set on the detection surface 311.

Transforming a detection surface coordinate system into an unity coordinate system will be described next with reference to FIGS. 8, 9, 10, and 11. The detection surface coordinate system is transformed into the unity coordinate system via a reference plane coordinate system. The detection surface coordinate system is a coordinate system associated with the images (detection surface) acquired by the flat panel detector 31. The detection surface coordinate system forms an X-Y orthogonal system. The X-axis of the detection surface coordinate system is defined by the abscissa of the top 103 (an axis perpendicular to a long axis Z1 and a vertical axis Z2). The Y-axis of the detection surface coordinate system is defined by the long axis Z1. An origin $O_0$ of the detection surface coordinate system coincides with the center of an image. The reference plane coordinate system is a coordinate system associated with an image projected on the reference plane 63. The reference plane coordinate system forms an X-Y orthogonal system. The X-axis of the reference plane coordinate system is defined by the abscissa of the top 103 (an axis perpendicular to the long axis Z1 and the vertical axis Z2). The Y-axis of the reference plane coordinate system is defined by the long axis Z1. An origin $O_1$ of the reference plane coordinate system coincides with the intersection between the imaging axis SID and the reference plane 63. Each of a plurality of images is defined by a corresponding reference plane coordinate system. The unity coordinate system forms an X-Y orthogonal system. The X-axis of the unity coordinate system is defined by the abscissa of the top 103 (an axis perpendicular to the long axis Z1 and the vertical axis Z2). The Y-axis of the unity coordinate system is defined by the long axis Z1. An origin $O_2$ of the unity coordinate system coincides with the intersection between the reference plane 63 and a perpendicular extending from a focus 221 to the reference plane 63. A plurality of images is defined by a single unity coordinate system. Let $(x_0, y_0)$ be the coordinates of a specific pixel PC on the detection surface coordinate system, $(x_1, y_1)$ be the coordinates of the specific pixel PC on the reference plane coordinate system, and $(x_2, y_2)$ be the coordinates of the specific pixel PC on the unity coordinate system. In addition, let L be the distance from the focus 221 to the detection surface 311 along the imaging axis SID, and H be the distance from the focus 221 to the reference plane 63 along the perpendicular 53.

FIG. 8 is a view showing the positional relationship between the detection surface 311 and the reference plane 63 concerning a long axis Z1 (y-axis) of the top 103. FIG. 9 is a view showing the positional relationship between the detection surface 311 and the reference plane 63 concerning the abscissa direction (x-axis) of the top 103. FIG. 10 is a view showing the position of the pixel of interest PC on the detection surface coordinate system. FIG. 11 is a view showing the position of the pixel of interest PC on the reference plane coordinate system.

The coordinates $(x_0, y_0)$ of the specific pixel PC on the detection surface coordinate system are transformed into the coordinates $(x_1, y_1)$ of the specific pixel PC on the reference plane coordinate system according to equations (4) and (5):

$$y_1 = \frac{y_0 \times H}{\cos\theta \times (y_0 \sin\theta + L\cos\theta)} \quad (4)$$

-continued $$x_1 = x_0 \times \frac{\sqrt{\left(\frac{H}{\cos\theta} - y_1\sin\theta\right)^2 + (y_1\cos\theta)^2}}{\sqrt{L^2 + y_0^2}} \quad (5)$$

The coordinates $(x_2, y_2)$ of the pixel of interest on the actual coordinate system are therefore defined by equations (6) and (7):

$$x_2 = x_0 \times \frac{\sqrt{\left(\frac{H}{\cos\theta} - \frac{y_0 \times H}{y_0\sin\theta + L\cos\theta}\tan\theta\right)^2 + \left(\frac{y_0 \times H}{y_0\sin\theta + L\cos\theta}\right)^2}}{\sqrt{L^2 + y_0^2}} \quad (6)$$

$$y_2 = \frac{y_0 \times H}{\cos\theta \times (y_0\sin\theta + L\cos\theta)} + H\tan\theta \quad (7)$$

The image processing unit 14 transforms the coordinates of each of a plurality of images arrayed along the long axis Z1 (Y-axis) from the detection surface coordinate system into the actual coordinate system by using the above coordinate transformation. Using the unity coordinate system allows the image processing unit 14 to unify the coordinates of a plurality of images into those in the single unity coordinate system. The unity coordinate system is used as a coordinate system in the combing processing to be described below.

Assume that a C-arm 101 is rotated while a rotation radius L of the flat panel detector 31 is fixed, and a plurality of (e.g., five) images is acquired. In this case, as shown in FIG. 12, the image processing unit 14 re-projects images 711, 712, 713, 714, and 715 onto the reference plane 63. When the C-arm 101 is rotated while the rotation radius L of the flat panel detector 31 is fixed, the widths of the fields of view of acquired images along the X-axis (axis A3) gradually decrease toward the middle along the Y-axis (axis A1). That is, the image 713 at the middle has a width D1min of the field of view which is the smallest among the images 711 to 715.

Upon performing re-projection, the image processing unit 14 combines the re-projected images 711 to 715, as shown in FIG. 12. Upon combing the images, the image processing unit 14 trims the images 711 to 715 according to a width D1min of the field of view of the image 713 to generate images 721, 722, 723, 724, and 725 having the same width D1min. That is, the image processing unit 14 trims the plurality of images 721 to 725 into rectangular shapes. Upon performing trimming, the image processing unit 14 combines the plurality of trimmed images 721 to 725 together to generate a long image having a rectangular shape. The width of the field of view of the generated long image along the X-axis is equal to the width D1min of the field of view of the image 713.

In order to increase the width of the field of view of each image to be acquired, the mechanism control unit 13 brings the flat panel detector 31 near to the top 103 during radiography. More specifically, as shown in FIG. 13, the mechanism control unit 13 brings the flat panel detector 31 near to the top 103 within a limited range in which the flat panel detector 31 does not interfere with the top 103. In this state, images are acquired via the flat panel detector 31. More specifically, the mechanism control unit 13 changes the rotational angle and rotation radius of the flat panel detector 31 such that a portion of the flat panel detector 31 which approaches most the top 103 (typically, one end portion of the flat panel detector 31 along the long axis Z1) is always positioned on a predetermined plane 65. The predetermined plane 65 is, for example, a plane which is positioned near the top 103 and is parallel to the top 103.

When images are acquired, the image processing unit 14 combines the acquired images. More specifically, as shown in FIG. 14, the image processing unit 14 re-projects acquired images 731, 732, 733, 734, and 735 onto the reference plane 63. In this case, the images 731 and 735 at the ends have a smallest width D2min of a field of view. Note that the width D2min of the field of view is larger than the width D1min of the field of view described above. That is, bringing the flat panel detector 31 near to the top 103 will prevent a reduction in the width of the field of view of the image 733 at the middle. In addition, always positioning an end portion of the flat panel detector 31 on the predetermined plane 65 will keep the width of the field of view on the side positioned on the predetermined plane 65 (the left side in FIG. 14) remain almost the same regardless of imaging positions. Upon performing re-projection, the image processing unit 14 trims the plurality of re-projected images 731 to 735 according to the same width D2min to generate images 741, 742, 743, 744, and 745 each having the width D2min of the field of view. Upon performing trimming, the image processing unit 14 combined the plurality of trimmed images 741 to 745 to generate a long image having a rectangular shape. The generated long image has the width D2min of the field of view. Bringing the flat panel detector 31 near to the top 103 in this manner can increase the width of the field of view of the long image along the X-axis.

Figure 15:
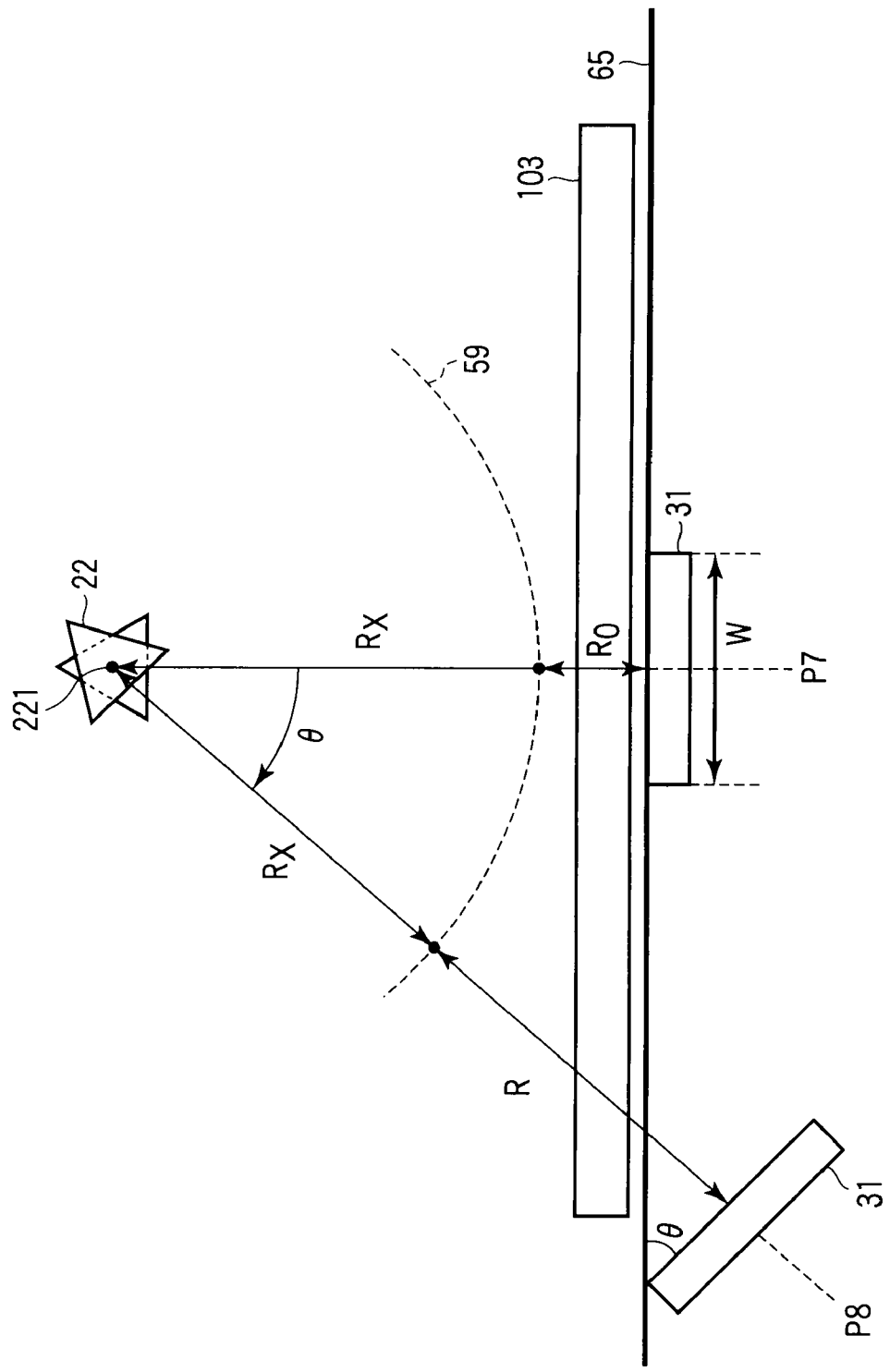
FIG. 15 is a view for explaining control of the rotation radius of the flat panel detector by the mechanism control unit according to the third embodiment.
Figure 17:
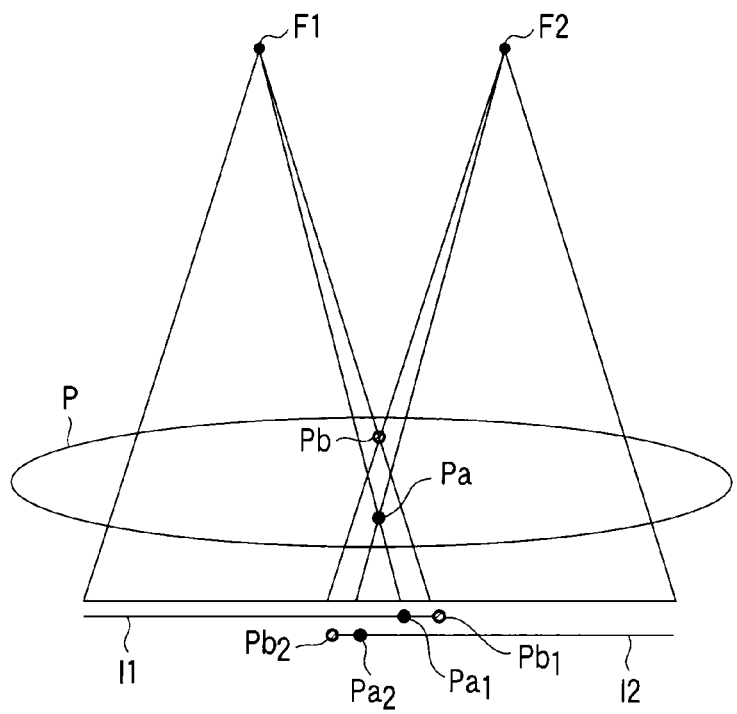
FIG. 17 is a view for explaining the disturbance of an image due to a difference in geometric enlargement ratio in a conventional X-ray diagnosis apparatus.
Figure 18:
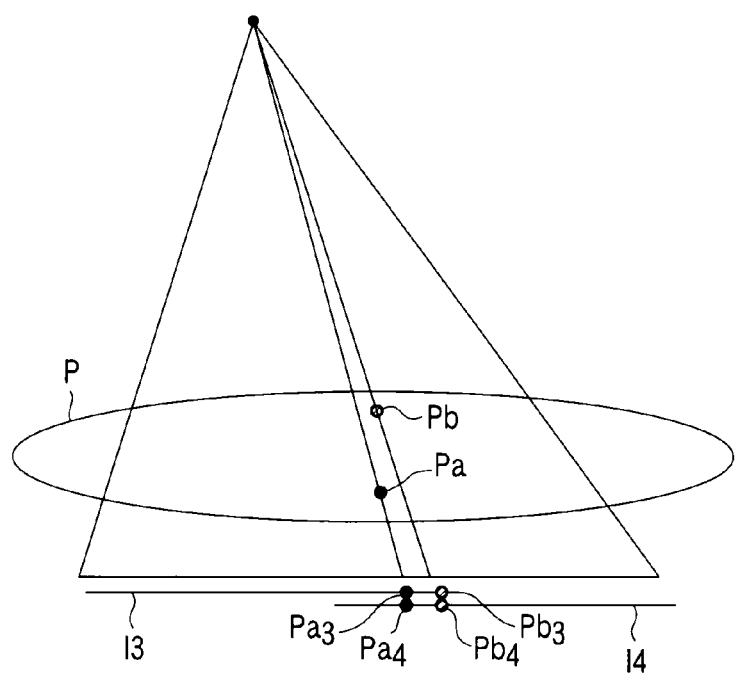
FIG. 18 is another view for explaining the disturbance of an image due to a difference in geometric enlargement ratio in the conventional X-ray diagnosis apparatus.

Control of the rotation radius R of the flat panel detector 31 by the mechanism control unit 13 will be described next with reference to FIG. 15. Let $R_0$ be the rotation radius of the flat panel detector 31 at a middle position P7, and W be the width of the flat panel detector 31 in the longitudinal direction. The mechanism control unit 13 controls the rotation radius R according to equation (8) to fix the distance interval between the top 103 and one end portion of the flat panel detector 31 along an axis A1 (long axis Z1).

$$R = \frac{R_X(1-\cos\theta) + R_0 + \frac{W}{2} \times \sin\theta}{\cos\theta}$$

A typical procedure of operation of the X-ray diagnosis apparatus 1 in bolus DSA will be described next with reference to FIG. 16.

Note that this bolus DSA is performed under the control of a system control unit 16. The overall operation of the X-ray diagnosis apparatus 1 is well known, and hence a description of the operation will be omitted.

In step S1, the system control unit 16 sets start point and end point for the execution of bolus DSA via an operation unit 12. The system control unit 16 determines an imaging interval (rotational angle) based on the set start point and end point. The system control unit 16 also determines acquisition trigger positions based on the determined imaging interval.

In step S2, the system control unit 16 determines the rotational speed of the C-arm 101. It is possible to freely change the rotational speed of the C-arm 101 in accordance with lever operation or the like by the operator.

In step S3, the system control unit 16 acquires a plurality of mask images by controlling the respective units. In this case, the mechanism control unit 13 controls the C-arm moving mechanism 104 and the C-arm rotating mechanism 105 so as to fix the position of a focus 221 and move the flat panel detector 31 on an arc orbit 57. Note that the arc orbit 57 has a rotation center coinciding with the focus 221. And the arc orbit 57 has a rotation radius equal to the length of the imaging axis SID as described above. The system control unit 16 causes the X-ray tube 22 to emit X-rays in response to the timing when the flat panel detector 31 crosses an acquisition trigger position and the acquisition timing of the flat panel detector 31 is set in a preparatory state (ready state). Note that in radiography, the rotational angle of the C-arm 101 and the rotation radius of the C-arm 101 (the X-ray tube 22 and the flat panel detector 31) at the time of image acquisition are recorded. In addition, the C-arm 101 need not stop at an acquisition trigger position but can continuously move. It is only required for adjacent mask images to contain an anatomically redundant area. In this manner, a plurality of mask images is acquired at a plurality of imaging positions.

In step S4, the system control unit 16 acquires a plurality of contrast images by controlling the respective units. Typically, the system control unit 16 acquires contrast images under the same control as that of the acquisition of the mask images. That is, the mechanism control unit 13 controls the C-arm holder 102 so as to fix the position of the focus 221 and move the flat panel detector 31 on the arc orbit 57. As the flat panel detector 31 moves on the arc orbit, a plurality of mask images and a plurality of contrast images can be regarded as being irradiated with X-rays from one focus 221. Note that the operator operates the operation unit 12 to change the rotational speed of the C-arm 101 while checking the flow of a contrast medium and the like. The system control unit 16 acquires a plurality of contrast images in accordance with the operation of the operation unit 12 by the operator. It is possible to arbitrarily change the moving direction of the C-arm 101 via the operation unit 12 in accordance with the flow of the contrast medium. The system control unit 16 causes the X-ray tube 22 to emit X-rays in response to the timing when the flat panel detector 31 crosses an acquisition trigger position and the acquisition timing of the flat panel detector 31 is set in a preparatory state (ready state). In addition, in radiography, the rotational angle of the C-arm 101 and the rotation radius of the C-arm 101 (the X-ray tube 22 and the flat panel detector 31) at the time of image acquisition are recorded.

In step S5, the system control unit 16 generates a long mask image and a long contrast image by controlling the image processing unit 14. The image processing unit 14 re-projects a plurality of mask images on a reference plane based on imaging information, and combines the plurality of re-projected mask images. This combing operation generates a long mask image based on the plurality of mask images. The image processing unit 14 corrects the overlapping positions between adjacent images in the process of combing by shifting pixels in accordance with an instruction from the operation unit 12. Likewise, the image processing unit 14 generates a long contrast image by combing a plurality of contrast images.

In step S6, the system control unit 16 generates the subtraction image between the long mask image and the long contrast image by controlling the image processing unit 14. More specifically, the image processing unit 14 positions the long mask image with the long contrast image based on imaging information. The image processing unit 14 then subtracts the long mask image from the positioned long contrast image. This subtracting operation generates a subtraction image. In this manner, the subtraction image associated with bolus DSA is generated.

Note that since uneven portions may sometimes be generated around images due to re-projection described above, it is preferable to generate a rectangular image by using an electronic mask.

As described above, the X-ray diagnosis apparatus 1 according to the third embodiment controls the C-arm holder 102 so as to fix the position of the focus 221 and move the flat panel detector 31 on the arc orbit 57. This makes it possible to regard all the positions of the focuses 211 concerning a plurality of mask images and a plurality of contrast images as the same position regardless of imaging positions. Therefore, this eliminates the necessity of the operation of strictly matching the imaging positions of mask images with those of contrast images, which operation has been required by the conventional apparatus to accurately combine images and accurately subtracting images. That is, the X-ray diagnosis apparatus 1 according to the third embodiment need not always acquire images at determined positions and is allowed to acquire mask images and contrast images at approximate positions (timings on the flat panel detector 31 side).

In addition, the X-ray diagnosis apparatus 1 is sometimes equipped with the flat panel detector 31 which cannot acquire images at irregular timings. Even in this case, the X-ray diagnosis apparatus 1 can obtain images regarded as having the same geometric enlargement ratio, and hence need not stop the X-ray tube 22 or the flat panel detector 31 at any specific positions.

Although the embodiments of the present invention have been described above, the present invention is not limited to the above embodiments. The embodiments can be variously modified and embodied within the spirit and scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnosis apparatus comprising:
an X-ray tube which generates X-rays;
a detector which detects X-rays generated by the X-ray tube and transmitted through a subject;
a C-arm which is equipped with the X-ray tube and the detector;
an arm support mechanism which rotatably supports the C-arm;
a top on which the subject is placed;
a first moving mechanism which supports the C-arm or the top so as to change a relative positional relationship along a horizontal direction between the C-arm and the top;
a second moving mechanism which supports the C-arm or the top so as to change a relative positional relationship along a vertical direction between the C-arm and the top; and
a control unit which controls the arm support mechanism, the first moving mechanism, and the second moving mechanism so as to a perpendicular extending from a focus of the X-ray tube intersects the top at a predetermined position thereon, and a distance interval between the X-ray tube and the predetermined position is fixed during rotation of the C-arm.

2. The apparatus according to claim 1, wherein the control unit controls the arm support mechanism, the first moving mechanism, and the second moving mechanism so as to move the detector on a first orbit having a predetermined rotation radius and move the top on a second orbit having the same diameter as the predetermined rotation radius.

3. The apparatus according to claim 1, wherein
the C-arm supports the detector so as to allow the detector to change a direction of an X-ray detection surface, and
the control unit controls the C-arm so as to make the detection surface parallel to the top regardless of a position of the detector.

4. The apparatus according to claim 3, wherein
the C-arm supports the detector so as to allow the detector to move along an axis connecting the focus and a center of the detection surface, and
the control unit controls the movement of the detection along the axis so as to make a length of a perpendicular extending from the focus to a plane containing the detection surface constant.

5. The apparatus according to claim 1, further comprising an image processing unit which projects data of images acquired via the detector onto a projection plane parallel to the top and generates data of the projected images.

6. The apparatus according to claim 1, wherein the control unit controls the C-arm support mechanism, the first moving mechanism, and the second moving mechanism so as to make geometric enlargement ratios of images acquired via the detector equal to each other regardless of imaging positions.

7. The apparatus according to claim 1, wherein the control unit controls the C-arm support mechanism, the first moving mechanism, and the second moving mechanism so as to make a relative positional relationship between the focus and the predetermined position remain unchanged.

8. An X-ray diagnosis apparatus comprising:
an X-ray tube which generates X-rays;
a detector which detects X-rays generated from the X-ray tube and transmitted through a subject;
a C-arm which is equipped with the X-ray tube and the detector;
an arm support mechanism which rotatably supports the C-arm;
a top on which the subject is placed;
a first moving mechanism which supports the C-arm or the top so as to change a relative positional relationship along a horizontal direction between the C-arm and the top;
a second moving mechanism which supports the C-arm or the top so as to change a relative positional relationship along a vertical direction between the C-arm and the top; and
a control unit which controls the arm support mechanism, the first moving mechanism, and the second moving mechanism so as to when a specific instruction is received from an operator, a perpendicular extending from a focus of the X-ray tube always intersects the top at a predetermined position thereon, a distance interval between the X-ray tube and the predetermined position is fixed, and the position of the focus is fixed in a space.

9. The apparatus according to claim 8, wherein
the C-arm supports the detector so as to allow the detector to change a direction of an X-ray detection surface, and
the control unit controls the C-arm so as to make the detection surface parallel to the top regardless of a position of the detector.

10. The apparatus according to claim 9, wherein
the C-arm supports the detector so as to allow the detector to move along an axis connecting the focus and a center of the detection surface, and
the control unit controls the movement of the detector along the axis so as to make a length of a perpendicular extending from the focus to a plane containing the detection surface constant.

11. The apparatus according to claim 8, further comprising an image processing unit which projects data of images acquired via the detector onto a projection plane parallel to the top and generates data of the projected images.

12. An X-ray diagnosis apparatus comprising:
an X-ray tube which generates X-rays;
a detector which detects X-rays generated from the X-ray tube and transmitted through a subject;
a top on which the subject is placed;
a C-arm which is equipped with the X-ray tube and the detector;
an arm support mechanism which rotatably supports the C-arm;
a moving mechanism which supports the C-arm or the top so as to change a relative positional relationship along a vertical direction between the C-arm and the top;
an image processing unit which generates a long mask image by combining a plurality of mask images acquired via the detector, generates a long contrast image by combining a plurality of contrast images acquired via the detector, and generates a subtraction image based on the long mask image and the long contrast image; and
a control unit which controls the arm support mechanism and the moving mechanism so as to fix a focus position of the X-ray tube, move the detector on an arc orbit at a predetermined distance from the focus position, and make imaging positions of the plurality of mask images and the plurality of contrast images differ from each other.

13. The apparatus according to claim 12, wherein the control unit controls the arm support mechanism and the moving mechanism so as to make imaging positions of each of the mask images differ from imaging positions of each of the contrast images.

* * * * *